(12) United States Patent
Darvish et al.

(10) Patent No.: US 9,018,174 B2
(45) Date of Patent: Apr. 28, 2015

(54) MOUSE MODEL AND TREATMENT OF HEREDITARY INCLUSION BODY MYOPATHY

(75) Inventors: Daniel Kohan Darvish, Sherman Oaks, CA (US); Yadira Valles-Ayoub, Woodland Hills, CA (US)

(73) Assignee: HIBM Research Group, Inc., Encino, CA (US)

( * ) Notice: Subject to any disclaimer, the term of this patent is extended or adjusted under 35 U.S.C. 154(b) by 1618 days.

(21) Appl. No.: 12/128,517

(22) Filed: May 28, 2008

(65) Prior Publication Data

US 2009/0298112 A1    Dec. 3, 2009

(51) Int. Cl.
*A61K 31/7012* (2006.01)
*A01K 67/027* (2006.01)
*G01N 33/573* (2006.01)

(52) U.S. Cl.
CPC ......... *A01K 67/0275* (2013.01); *A01K 2217/00* (2013.01); *A01K 2227/105* (2013.01); *A01K 2267/03* (2013.01); *G01N 33/573* (2013.01); *G01N 2333/91215* (2013.01); *G01N 2333/99* (2013.01); *G01N 2500/10* (2013.01)

(58) Field of Classification Search
CPC .................................................. A61K 31/7012
USPC ........................................................... 514/23
See application file for complete search history.

(56) References Cited

FOREIGN PATENT DOCUMENTS

WO    WO 2008/150477    * 12/2008

OTHER PUBLICATIONS

Sparks et al. (2004) BMC Neurology, vol. 7(3), 1-13.*
Noguchi et al. (2004) J. Biol. Chem., vol. 279(12), 11402-11407.*
Charter et al., Biosynthetic incorporation of unnatural sialic acids into polysialic acid on neural cells. Glycobiology 2000; 10: 1049-1056.
Luchansky et al., GlcNAc 2-epimerase can serve a catabolic role in sialic acid metabolism. J Biol. Chem. 2003; 278: 8035-8042.
Schwarzkopf et al., Sialylation is essential for early development in mice. Proc. Natl. Acad. Sci. USA. 2002; 99:5267-5270.
Bardor, M. et al., "Mechanism of Uptake and Incorporation of the Non-human Sialic Acid N-Glycolylneuraminic Acid into Human Cells," The Journal of Biological Chemistry, 280(6):4228-4237 (2005).
Duncan, P. I. et al., "Sialic Acid Utilisation and Synthesis in the Neonatal Rat Revisited," PLoS ONE, 4(12):e8241 (2009).
Kell, D. B. et al., "The Cellular Uptake of Pharmaceutical Drugs is Mainly Carrier-Mediated and is Thus an Issue not so Much of Biophysics but of Systems Biology," Beilstein-Institut, Systems Chemistry, May 26-30, 2008, Bozen, Italy, pp. 149-168.
Qin, L. et al., "Sialin (SLC17A5) functions as a nitrate transporter in the plasma membrane," PNAS, 109(33):13434-13439 (2012).
Wreden, C. C. et al., "Varied Mechanisms Underlie the Free Sialic Acid Storage Disorders," The Journal of Biological Chemistry, 280(2):1408-1416 (2005).

* cited by examiner

*Primary Examiner* — Anne Marie S Wehbe
(74) *Attorney, Agent, or Firm* — Cooley LLP

(57) ABSTRACT

Disclosed herein are methods of treating HIBM in a subject comprising identifying subject in need thereof, and administering to the subject a compound, or a pharmaceutically acceptable salt, ester, amide, glycol, peptidyl, or prodrug thereof, wherein the compound is a compound that is biosynthesized in a wild type individual along a biochemical pathway between glucose and sialic acid, inclusive. Also disclosed herein are vectors comprising a nucleic acid sequence that encodes a polypeptide having at least 80% sequence identity to the sequence set forth in SEQ ID NO:2, recombinant cells comprising these vectors, and recombinant animals comprising the cells. In addition, methods of identifying a compound having therapeutic effect for HIBM are disclosed.

4 Claims, 2 Drawing Sheets

| | BUN (mg/dL) | Creatinine (mg/dL) | Creatine Kinase (U/L) |
|---|---|---|---|
| +/+ [a] | 21 (SD ± 2.1) | 0.33 (SD ± 0.10) | 410 (SD ± 308) |
| +/- [a] | 18.3 (SD ± 2.3) | 0.33 (SD ± 0.10) | 525 (SD ± 482) |
| -/- [b] | 39 (SD ± 10.4) | 0.45 (SD ± 0.17) | 575 [c] |

[a] 3 animals, n=9; [b] one animal, n=3; [c] n=2.

MOUSE MODEL AND TREATMENT OF HEREDITARY INCLUSION BODY MYOPATHY

FIELD OF THE INVENTION

The present invention is in the field of treatment of Hereditary Inclusion Body Myopathy and genetically modified mice as test models for the same.

BACKGROUND OF THE DISCLOSURE

Hereditary Inclusion Body Myopathy (HIBM, MIM 600737) is an autosomal recessive neuromuscular disorder characterized by adult onset, slowly progressive muscle weakness and atrophy. Serum creatine kinase levels are normal to slightly elevated and electromyograms show either a myopathic or a neuropathic pattern. Histologically, muscle fibers degenerate and develop cytoplasmic rimmed vacuoles and cytoplasmic or nuclear filamentous inclusions. No therapy currently exists for HIBM.

The myopathy results from mutations in GNE gene, coding for the bifunctional enzyme UDP-N-acetylglucosamine (GlcNAc) 2-epimerase/N-acetylmannosamine (ManNAc) kinase (GNE/MNK). A GNE founder mutation (M712T) was originally described in Persian-Jewish HIBM families, but numerous other mutations in GNE are now reported in patients worldwide. GNE/MNK is ubiquitously expressed and catalyzes the first two committed, rate-limiting steps in the biosynthesis of N-acetylneuraminic acid (Neu5Ac, sialic acid). The enzyme is feedback-inhibited by the downstream product, CMP-Neu5Ac. Neu5Ac is the most abundant mammalian sialic acid and is typically found as the terminal sugar on glycoconjugates, where it plays a role in a variety of cellular signaling functions. HIBM-associated GNE mutations, result in reduced activity of both GlcNAc 2-epimerase and ManNAc kinase activities; these decrements are considered responsible for reduced production of sialic acid.

The pathologic mechanism of the eventual muscle fiber degeneration of HIBM remains unknown. However, evidence suggests that decreased availability of sialic acid in muscle causes hyposialylation of muscle glycoproteins, whether involving glycans in general, O-linked glycans, polysialic acid on neural cell adhesion molecule (PSA-NCAM), or specific O-mannosylated glycosyl residues on α-dystroglycan. The O-mannosylated residues on α-dystroglycan govern interactions of α-dystroglycan with extracellular matrix proteins, and their deficiency is responsible for several congenital muscular dystrophies, including Walker-Warburg syndrome and Muscle-Eye-Brain disease.

While the above pathways that are implicated in the disease are known, no treatment for the disease has been found to date. Therefore, there is a need in the art for animal models in which the disease can be studied, and treatment regimens that can ameliorate the effects of the disease.

SUMMARY OF THE INVENTION

Disclosed herein is a vector comprising a nucleic acid sequence that encodes a polypeptide having at least 80% sequence identity to the sequence set forth in SEQ ID NO:2. In some embodiments, the polypeptide has a sequence selected from the group consisting of set forth in SEQ ID NO:2 through SEQ ID NO:19.

Also disclosed herein is a recombinant cell comprising the vector wherein the vector comprises a nucleic acid sequence that encodes a polypeptide having at least 80% sequence identity to the sequence set forth in SEQ ID NO:2. In some of these embodiments, the polypeptide has a sequence selected from the group consisting of set forth in SEQ ID NO:2 through SEQ ID NO:19. In certain embodiments, the cell is a stem cell, which can be an embryonic stem cell. Some of the stem cells are murine.

Further, disclosed herein is a recombinant animal where the animal has a cell that expresses a polypeptide having at least 80% sequence identity to the sequence set forth in SEQ ID NO:2. In some embodiments, the animal is made by the process of producing a vector comprising a nucleic acid sequence that encodes a polypeptide having at least 80% sequence identity to the sequence set forth in SEQ ID NO:2; producing a recombinant mammalian embryonic stem cell by infecting a mammalian embryonic stem cell with the vector; selecting the embryonic stem cell line that has undergone homologous recombination to incorporate the vector sequence at a desired genomic locus; planting the recombinant stem cell in an embryo; implanting the embryo in a female animal; and allowing the implanted embryo to mature into a fully formed fetus and be born from the female animal. In some of these embodiments, the polypeptide has a sequence selected from the group consisting of set forth in SEQ ID NO:2 through SEQ ID NO:19. In certain embodiments, the animal comprises two alleles of the gene that encodes a polypeptide having a sequence set forth in SEQ ID NO:2. In other embodiments, the animal comprises one allele of the gene that encodes a polypeptide having a sequence set forth in SEQ ID NO:2, and another allele of the gene that encodes a polypeptide having a sequence set forth in SEQ ID NO:3-19. In yet other embodiments, the animal comprises two alleles of the gene that each independently encodes a polypeptide having a sequence set forth in SEQ ID NO:3-19.

Also disclosed herein is a method of identifying a compound having therapeutic effect for HIBM, the method comprising administering the compound to a recombinant cell; and measuring the effect of the compound on a rate of production, or an extent of production, of sialic acid or CMP-sialic acid by the cell, where the recombinant cell comprising a nucleic acid sequence that encodes a polypeptide having at least 80% sequence identity to the sequence set forth in SEQ ID NO:2. In some embodiments, the recombinant cell comprises the vector, wherein the vector comprises a nucleic acid sequence that encodes a polypeptide having at least 80% sequence identity to the sequence set forth in SEQ ID NO:2. In some of these embodiments, the polypeptide has a sequence selected from the group consisting of set forth in SEQ ID NO:2 through SEQ ID NO:19. In some of these embodiments, the recombinant cell is in vitro. In other embodiments, the recombinant cell is a cell of a recombinant animal. In some of these embodiments, the recombinant cell is in vivo. In certain embodiments, the recombinant animal is made by the process of producing a vector comprising a nucleic acid sequence that encodes a polypeptide having at least 80% sequence identity to the sequence set forth in SEQ ID NO:2; producing a recombinant mammalian embryonic stem cell by infecting a mammalian embryonic stem cell with the vector; selecting the embryonic stem cell line that has undergone homologous recombination to incorporate the vector sequence at a desired genomic locus; planting the recombinant stem cell in an embryo; implanting the embryo in a female animal; and allowing the implanted embryo to mature into a fully formed fetus and be born from the female animal.

DETAILED DESCRIPTION OF THE EMBODIMENTS

Figure 1:
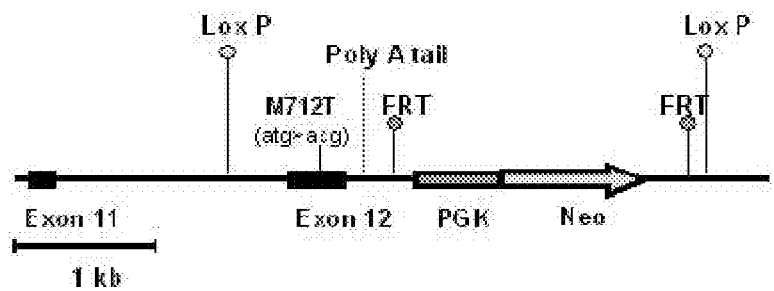
FIG. 1 is a scheme showing the resultant murine GNE (Uea1) genomic locus, exons 11 and 12, after homologous recombination with the targeting vector. The M712T missense mutation was created in exon 12 and a neo cassette (under the PGK promoter) was inserted, flanked by FRT sites. LoxP sites were inserted before exon 12 and after the PGK-neo gene.

In one aspect, disclosed herein is a method of treating HIBM in a subject comprising identifying subject in need thereof and administering to the subject a compound, or a pharmaceutically acceptable salt, ester, amide, glycol, peptidyl, or prodrug thereof, wherein the compound is a compound that is biosynthesized in a wild type individual along the pathway between glucose and sialic acid, inclusive.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound disclosed herein with inorganic acids such as hydrochloric acid, hydrobromic acid, sulfuric acid, nitric acid, phosphoric acid, or organic acids such as methanesulfonic acid, ethanesulfonic acid, p-toluenesulfonic acid, salicylic acid and the like. Pharmaceutical salts can also be obtained by reacting a compound disclosed herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a compound disclosed herein, thereby forming a prodrug.

Any amine, hydroxy, or carboxyl side chain on the compounds disclosed herein can be esterified or amidified. The procedures and specific groups to be used to achieve this end is known to those of skill in the art and can readily be found in reference sources such as Greene and Wuts, Protective Groups in Organic Synthesis, 3.sup.rd Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound disclosed herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In some embodiments, the compound is UDP-GlcNAc. In other embodiments, the compound is ManNAc. In yet other embodiments, the compound is ManNAc-6-P. In further embodiments, the compound is NeuAc-9-P. In some embodiments, the compound is sialic acid.

In some embodiments, provision of free sialic acid attenuates the hyposialylation in HIBM muscle and ameliorates the myopathic symptoms. In some of these embodiments, sialic acid is administered in its free form, bound as glycoconjugates, or as its precursor, ManNAc, which is uncharged and crosses membranes readily.

ManNAc is also situated in the sialic acid biosynthesis pathway after the rate-limiting UDP-GlcNAc 2-epimerase step, so its metabolism is not subject to feedback inhibition. In some embodiments, residual ManNAc kinase activity in HIBM patients, or ancillary kinases such as GlcNAc kinase, converts ManNAc into ManNAc-6P for subsequent synthesis of sialic acid. In fact, hyposialylated, GNE-deficient mouse embryonic stem cells became resialylated after their growth medium was supplemented with ManNAc [Schwarzkopf, 2002]. Furthermore, incubation of cultured cells with 'unnatural' ManNAc derivatives (ManLev, N-levulinoylmannosamine or ManNAz, N-azidoacetylmannosamine) resulted in incorporation of the downstream sialic acid analogs, Sia-Lev or SiaNAz, into cell surface glycoconjugates [Luchansky, 2003; Charter, 2002].

It is useful to test therapeutic methods involving the provision of sialic acid, or other therapeutic compounds, in animal models of HIBM. Animal models are developed by creating a knock-in animal model having a homozygous for the classic M712T mutation.

Thus, in another aspect, disclosed herein is a vector comprising a sequence set forth in SEQ ID NO:1. In some embodiments, the vector comprises a mutated gene. In some of these embodiments, the mutation is M712T mutation. By a gene having a, for example, M712T mutation it is meant that the gene encodes a polypeptide having the sequence set forth in SEQ ID NO:2, except that the methionine at position 712 is replaced with a threonine. In other embodiments, the mutation is selected from the group consisting of R8X, R71W, I142T, W204X, V216A, R246Q, I298T, R335W, Q436X, L556S, V572L, I587T, S615X, A631V, Y675H, and V696M.

In another aspect, disclosed herein is a vector comprising a gene, wherein the gene encodes a polypeptide having a sequence set forth in SEQ ID NO:2, or a polypeptide having at least 80% sequence identity to the sequence set forth in SEQ ID NO:2. In some embodiments, the encoded polypeptide has at least at least 85% sequence identity to the sequence set forth in SEQ ID NO:2. In other embodiments, the encoded polypeptide has 90% sequence identity to the sequence set forth in SEQ ID NO:2. In other embodiments, the encoded polypeptide has at least 95% sequence identity to the sequence set forth in SEQ ID NO:2. In other embodiments, the encoded polypeptide has at least 99% sequence identity to the sequence set forth in SEQ ID NO:2.

In some embodiments, the vector comprises a gene, wherein the gene encodes a polypeptide having a sequence set forth in SEQ ID NO:2, except that the polypeptide comprises a mutation selected from the group consisting of R8X (SEQ ID NO:3), R71W (SEQ ID NO:4), I142T (SEQ ID NO:5), W204X (SEQ ID NO:6), V216A (SEQ ID NO:7), R246Q (SEQ ID NO:8), I298T (SEQ ID NO:9), R335W (SEQ ID NO:10), Q436X (SEQ ID NO:11), L556S (SEQ ID NO:12), V572L (SEQ ID NO:13), I587T (SEQ ID NO:14), S615X (SEQ ID NO:15), A631V (SEQ ID NO:16), Y675H (SEQ ID NO:17), V696M (SEQ ID NO:18), and M712T ((SEQ ID NO:19). By a polypeptide having a, for example, M712T mutation it is meant that the polypeptide has the sequence set forth in SEQ ID NO:2, except that the methionine at position 712 is replaced with a threonine. The R8X mutation incorporates a stop codon. The resulting expressed polypeptide will only have the first seven amino acids of the SEQ ID NO:2.

In another aspect, disclosed herein is a recombinant cell comprising the vector described above. In some embodiments, the recombinant cell is a stem cell. In some of these embodiments, the recombinant cell is an embryonic stem cell. In some embodiments, the recombinant cell is a mammalian cell. In some embodiments, the recombinant cell is a mammalian stem cell, which can be a mammalian embryonic stem cell. In some embodiments, the mammal is selected from the group consisting of mouse, rat, rabbit, guinea pig, dog, cat, sheep, goat, cow, horse, monkey, chimpanzee, and ape. In some embodiments, the mammal is a primate. In other embodiments, the mammal is a murine.

In another aspect, disclosed herein is a recombinant animal comprising a recombinant cell described above. In some embodiments, the animal is a mammal. In some of these embodiments, the mammal is selected from the group consisting of mouse, rat, rabbit, guinea pig, dog, cat, sheep, goat, cow, horse, monkey, chimpanzee, and ape. In some embodiments, the mammal is a primate. In other embodiments, the mammal is a murine.

In another aspect, disclosed herein is a recombinant animal made by the process of:
producing a vector comprising a nucleic acid sequence that encodes a polypeptide selected from the group consisting of SEQ ID NO:2-19;
producing a recombinant mammalian embryonic stem cell by infecting a mammalian embryonic stem cell with the vector;
selecting the embryonic stem cell line that has undergone homologous recombination to incorporate the vector sequence at a desired genomic locus;
planting the recombinant stem cell in an embryo;
implanting the embryo in a female animal; and
allowing the implanted embryo to mature into a fully formed fetus and be born from the female animal.

FIG. 1 is a schematic depiction of the genomic locus where the homologous recombination to incorporate the vector sequence is desired to undergo.

In some embodiments, the recombinant animal comprises one allele encoding for SEQ ID NO:2 and another allele encoding for a polypeptide selected from the group consisting of SEQ ID NO:3-19. In another embodiment, in the recombinant animal both alleles encode for a polypeptide selected from the group consisting of SEQ ID NO:3-19.

In another aspect, disclosed herein is a method of identifying a compound having therapeutic effect for Hereditary Inclusion Body Myopathy (HIBM), the method comprising: administering the compound to a recombinant cell; and measuring the effect of the compound on a rate of production, or an extent of production, of sialic acid or CMP-sialic acid by the cell, where the recombinant cell comprises a nucleic acid sequence that encodes a polypeptide having at least 80% sequence identity to the sequence set forth in SEQ ID NO:2.

In some embodiments, the recombinant cell comprises a vector, where the vector comprises a nucleic acid sequence that encodes a polypeptide having at least 80% sequence identity to the sequence set forth in SEQ ID NO:2. In some of these embodiments, the polypeptide has a sequence selected from the group consisting of set forth in SEQ ID NO:2 through SEQ ID NO:19.

In some embodiments, the recombinant cell is in vitro. In these embodiments, a particular cell is transformed and the cell is used in assays to identify therapeutic compounds without the cell being a part of a recombinant animal. The cell is, for example, used in standard and known cellular assays that detect the expression of polypeptides in cells in vitro.

In other embodiments, the recombinant cell is a cell of a recombinant animal. In some of these embodiments, the cell is part of a recombinant animal, or a tissue obtained from a recombinant animal. Thus, in these embodiments, the recombinant cell is in vivo. In some embodiments, the recombinant animal is made by the processes disclosed herein.

There are many well-known methods in the art to measure the therapeutic effect of a compound. In some ways, the same criterion is measured before and after the administration of the compound and the two measurements are compared. In other embodiments, a number of subjects are divided into at least two groups, where one receives the compound and the other receives a placebo, the same criterion is measured in the two groups, and the two measurements are compared. The criterion can be, for example, muscle movement, limb movement, muscle growth, muscle stamina, muscle fatigability, muscle strength, muscle tensile force, muscle atrophy, neuronal atrophy, life-span, extent of activity, and the like.

The terms "treating," "treatment," and "therapeutic" do not necessarily mean total cure. Any alleviation of any undesired signs or symptoms of the disease to any extent or the slowing down of the progress of the disease can be considered treatment. Furthermore, treatment may include acts that may worsen the aptient's overall feeling of well being or appearance. Treatment may also include lengthening the life of the subject, even if the symptoms are not alleviated, the disease conditions are not ameliorated, or the subject's overall feeling of well being is not improved.

In one particularly preferred embodiment, a gene-targeted knock-in mouse model homozygous for the classic M712T mutation was created. This mouse died within 72 hours after birth, at which time a muscle phenotype was not present. Instead, homozygous mice had severe glomerular disease, including fusion of the podocyte slit diaphragm membranes, possibly due to hyposialylation of specific membrane glycoproteins. Administration of ManNAc to pregnant mothers had a remarkably salutary effect on survival of homozygous pups and was associated with increased sialylation of PSA-NCAM as well as increased expression of GNE/MNK protein and its epimerase activity, suggesting that ManNAc might be stabilizing the mutant enzyme.

EXAMPLES

The following examples are only illustrative of some of the embodiments of the invention disclosed herein and are not meant to limit the invention in any form.

Example 1

Methods

GNE-M712T mice. GNE-M712T knock-in mice were generated by targeting the M712T (ATG>ACG) mutation exon 12 of the murine GNE gene (Uae1, Gne, GenBank NM_015828). The mutant mice were maintained in the C57BL/6J background. Animals were housed in ventilated cages in a temperature- and light-controlled environment (22° C., 30-70% humidity, 12-hour light/12-hour dark cycle) and were fed irradiated chow (Prolab 5P75 Isopro 3000; PMI Nutrition International) and water ad libitum. All euthanasia was performed with by $CO_2$ followed by cervical dislocations. For Mendelian distribution studies, four pregnant mice E17-19 were euthanized and embryos were retrieved by cesarean section and euthanized by decapitation. All mouse procedures were performed in accordance with protocol G04-3 approved by the Institutional Animal Core and Use Committee of the National Human Genome Research Institute, National Institutes of Health Institutional Review Board.

Molecular analysis. Mouse genotyping was performed on tail genomic DNA or cDNA isolated from murine kidney or skeletal muscle using standard protocols. Total RNA was isolated from murine tissues using the TRIzol reagent (Invitrogen Life Technologies), and cDNA was prepared using the SuperScript III system (Invitrogen Life Technologies). PCR amplifications were performed across the M712T mutation with genomic DNA as template, using the primerset 5'-AGCACTTCCTGGAGTTTGATG-3' (SEQ ID NO:20) and 5'-ATTTGCCTTCGCAGAAACACTTGA-3' (SEQ ID NO:21) or with cDNA as template using the primerset 5'-GCCCAGAGCATCTTACGAAC-3' (SEQ ID NO:22) and 5'-GGGTCCCCTGGAGCTTGG-3' (SEQ ID NO:23) and PuReTaq Ready-To-Go PCR beads (Amersham Biosciences), using standard PCR conditions. PCR fragments were digested with Nla III at 37° C. to verify the mutation status. Quantitative real-time PCR was performed on RNA isolated from kidney and skeletal muscle, utilizing assays-on-demand (Applied Biosystems) for GNE (mm00607939_s1) and β-actin (mm00450174_m1) on an ABI PRISM 7900 HT Sequence Detection System (Applied Biosystems).

Clinical Chemistry Screen. Blood samples (100-150 μl) from weaned, sex (male) and age (starting at age 6 months) matched mice (weighing at least 15 grams) were obtained bimonthly, by puncture of anesthetized retro-orbital sinus (0.5% tetracaine HCl, Bausch and Lomb Pharmaceuticals). Samples were allowed to clot (30 min, room temperature) in MicroPrep centrifuge tubes (StatSpin), after which the serum was separated by centrifugation at 1500 g for 10 min, and stored at −80° C. until analysis. Clinical Chemistry screens were performed at the Department of Laboratory Medicine at the National Institutes of Health (http://www.cc.nih.gov/cp/index.shtml) and included monitoring of creatinine, blood urea nitrogen (BUN), albumin, total protein, uric acid, alkaline phosphatase, alanine aminotransferase (ALT), aspartate aminotransferase (AST), amylase, creatine kinase and lactate dehydrogenase. In addition, reagent strips for protein urinalysis were used to assess proteinuria in urine from mice (Chemstrip 2GP; Roche).

Antibodies. A rabbit polyclonal antibody was custom prepared against a GNE/MNK peptide comprising amino acids 588-607: EAYASGMALQREAKKLHDED (SEQ ID NO:24), coupled to keyhole limpet hemocyanine (KLH) and affinity-purified against the corresponding antigenic peptide (Covance). Other primary antibodies were commercially obtained: dystrophin (ab15277, AbCam), α-dystroglycan (IIH6, Upstate Biotechnology), laminin (L9393, Sigma-Aldrich), podocalyxin (PODX15-A, Alpha Diagnostic International), PSA-NCAM (MAB5324, Chemicon), and β-actin (AAN01, Cytoskeleton).

Mouse Histology. Mouse tissues were collected, formalin-fixed and paraffin-embedded. Tissue sections (5 μm) were prepared and stained with hematoxylin and eosin following standard procedures (American Histolabs) or subjected to immunohostochemistry with a variety of primary antibodies. Formalin fixed tissues were deparafinized in Histoclear II (National Diagnostics), dehydrated in a series of ethanol solutions. Antigen retrieval was performed for sections to be stained with the antibodies GNE/MNK (5 min boiling in citric acid based solution; Vector Laboratories) and dystrophin (boiling in 1 mM EDTA, according the manufacturer's protocol; AbCam). The sections were blocked (2% BSA, 10% donkey serum and 0.1% Triton X-100 in PBS) and incubated with primary antibodies (GNE/MNK 1:50; laminin 1:25; dystrophin 1:50) overnight at 4° C., followed by the secondary antibody Alexa 488 donkey-anti-rabbit (1:500 in blocking solution) (Invitrogen). The sections were mounted in Vectashield (Vector Laboratories) and viewed and digitally imaged with a Zeiss Axiovert 200M microscope (Carl Zeiss, Microimaging).

Western blotting. Mouse tissues (age P2) were extracted, homogenized in CelLytic buffer, consisting of a mild detergent, bicine buffer and 150 mM NaC (CelLytic) supplemented with protease inhibitors (Complete Minia, Roche). The lysates were sonicated and cleared by centrifugation (1000 g for 10 min), and the resulting supernatants were assayed for protein concentration (BCA protein assay, Pierce). For the neuraminidase enzymatic treatments, protein homogenates (25 μg) were incubated with 1 mU/μg of Neuraminidase (N-6514, Sigma) for 30 min at 37° C. Equal amounts of protein (25-50 μg) were electrophoresed on 4-12% Tris-Glycine gels (Novex, Invitrogen), and electroblotted onto 0.45 μm Hybond ECL nitrocellulose membranes (Amersham Pharmacia Biotech). The membranes were blocked (10% fat-free milk) and incubated with primary antibodies, followed by incubation with HRP-conjugated secondary antibodies (Amersham Biosciences). Results were visualized with enhanced chemiluminescence (ECL Western Blotting Detection Reagents, Amersham Biosciences) and exposure to CL-XPosure film (Pierce Biotechnology). Densitometry was performed on the digital images obtained with a Kodak Image station and software (Perkin Elmer). The protein levels were normalized to those of β-actin to correct for differences in protein loading and/or transfer.

Electron Microscopy. Kidney tissues were fixed overnight at 4° C. in 2% glutaraldehyde in 0.1M cacodylate buffer (pH 7.4), followed by washing with cacodylate buffer and post-fixation with 1% $OSO_4$ for 2 h. After washing (0.1 M cacodylate buffer), the tissues were serially dehydrated in ethanol and embedded in Eponate 12 resin (Ted Pella). Thin sections (~80 nm), were obtained by a Leica ultracut-UCT ultramicrotome (Leica), placed onto 400 mesh copper grids, and stained with saturated uranyl acetate in 50% methanol, followed by lead citrate. The grids were viewed with a Philips 410 electron microscope (FEI Company) at 80 kV and images were recorded on Kodak SO-163 film (Kodak).

ManNAc administration. Breeding pairs of 6-week-old +/− mice were divided into three groups. Group I consisted of 9 +/− breeding pairs who were administered untreated sterilized tap water. Group II consisted of one breeding pair of +/+ mice (wild-type control) and 6 +/− breeding pairs who were administered 1 mg/ml ManNAc (Sigma) supplemented water. Group III consisted of one +/+ breeding pair and 7 +/− breeding pairs who were administered 5 mg/ml ManNAc supplemented water. Water was changed twice weekly. Nursing females continued to be supplied with ManNAc. All mice were weaned from ManNAc at 21 days. Selected whole litters were sacrificed at age P2 or P6 for histological, genetic, biochemical or ultrastructural analysis.

GNE/MNK enzymatic assays. Mouse kidney and skeletal muscle (hindlimb quadriceps) tissues were homogenized and subjected to the GNE/MNK epimerase enzymatic assay as described[11,44]. This assay is based on incubation with radiolabeled substrate (UDP-[$^3$H]GlcNAc; American Radiolabeled Chemicals), and detection of radiolabeled product ([$^3$H]ManNAc) upon separation of oligosaccharides by high pH anion-exchange chromatography with pulsed amperometric detection (Dionex).

Statistical analysis. Differences in genotype distribution (+/+: +/−---/−) between an untreated control group and ManNAc treated group were tested by a two-tailed Fisher's exact test. To this end a 2×3 table was generated.

Example 2

Generation and Examination of GNE-M712T Knock-in Mice

Figure 2:
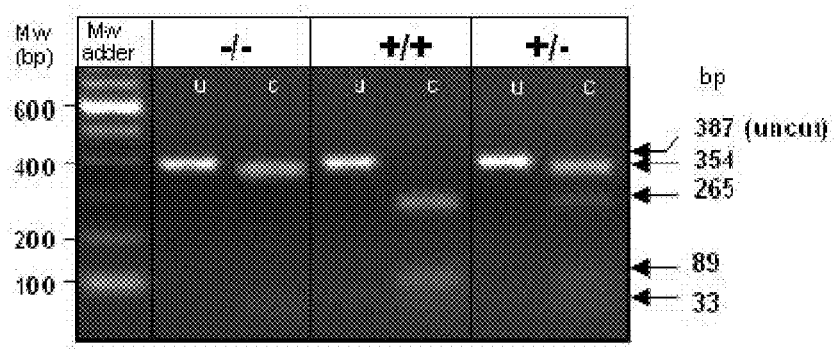
FIG. 2 is a photograph of a gel showing the genotyping of mutant mice. PCR amplification of genomic DNA across the M712T (ATG>ACG) mutation site yielded a 387-bp fragment that was digested by the NlaIII restriction endonuclease into 354-bp and 33-bp fragments in a normal allele (+) and into 265-bp, 89-bp and 33-bp in the mutant allele (−).
Figure 3:
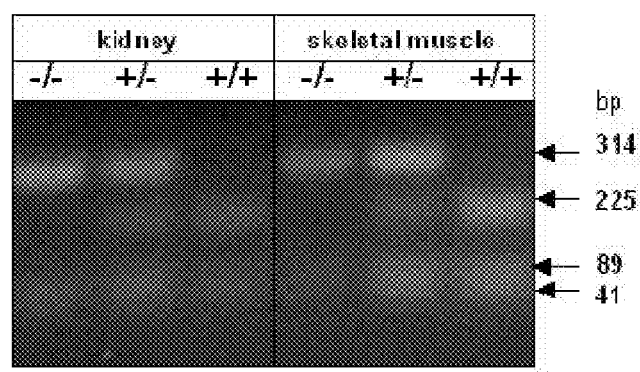
FIG. 3 is a photograph of a gel showing the results of RT-PCR of kidney and skeletal muscle RNA. RNA was reverse transcribed onto cDNA and amplified by PCR with primers covering exons 11 and 12 (355-bp). Digestion by NlaIII cuts the normal allele (+) into 225-bp, 89-bp, and 41-bp fragments; the M712T allele (−) is cut into 314-bp and 41-bp fragments. Digestion confirmed the exclusive presence of the normal allele in +/+tissues, both alleles in +/− tissues, and only the M712T allele in −/− tissues.

A murine targeting vector for homologous recombination in C57BL/6J embryonic stem cells was constructed including the M712T GNE mutation (FIG. 1). The neo (neomycin phosphotransferase) and tk (thymidine kinase) genes were introduced into the vector as positive and negative selection markers, respectively (FIG. 1). Additional LoxP (flanking exon 12 and neo) and FRT (flippase recombinase target) sites (flanking neo) were inserted for potential future conditional transgenic models. Genotyping of the mice was performed by PCR amplification and digestion with the restriction endonuclease NlaIII (FIG. 2). Tissues of homozygous mutated (−/−) mice and wild type mice (+/+) showed comparable GNE RNA transcript levels by real-time PCR (not shown). Furthermore, NlaIII digestion of amplified cDNA demonstrated homozygous insertion of the M712T mutation in RNA of −/− mice (FIG. 3).

Early Postnatal Lethality of −/− Mice

Figures 4, 5:
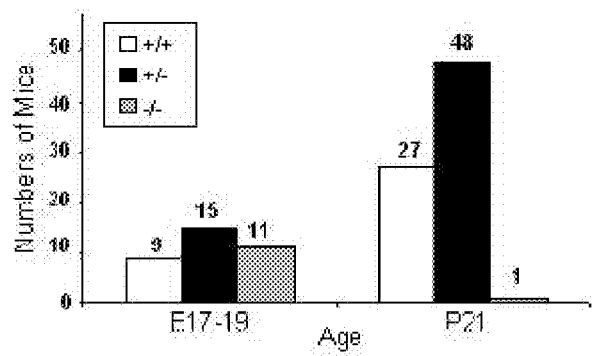
FIG. 4 is a graph showing numbers of mice at embryonic age E17-19 and at weaning age P21. At P21, genotyping of 76 mice from 13 litters (9 +/− matings) identified only one −/−offspring. Subsequent genotyping of 35 E17-19 embryos from 4 +/− matings yielded a Mendelian distribution of genotypes.
FIG. 5 is a table disclosing serum metabolite levels in weaned male mice, measured biweekly between age 6-8 months. BUN=Blood Urea Nitrogen.

Initial matings of heterozygous (+/−) mice yielded only one −/− animal at weaning age (postnatal day 21; P21). However, subsequent genotyping of 35 embryos at day E17-19 showed 26% (+/+): 43% (+/−): 31% (−/−) in utero, equaling a Mendelian distribution, statistically confirmed by goodness of fit testing ($\chi^2=0.94$, $P=0.62$) (FIG. 4). At E17-19, the embryos displayed normal exteriors, normal head and body sizes, and normal pink skin, indicating good circulatory and respiratory function. By P2, however, −/− mice appeared slightly smaller, with weights 70-100% of those of control littermates. The −/− mice stomachs contained milk upon dissection, although a milkspot was not always visible. By P3, all −/− mice except one had died. In contrast, +/− mice appeared entirely unaffected.

Serum metabolite analyses of weaned mice revealed elevated blood urea nitrogen (BUN) levels and excessive amounts of urinary protein for the −/− mice, indications of renal disease (FIG. 5). Blood creatinine levels were within the normal range in all genotypes and creatine kinase levels were normal to slightly elevated in −/− mice (FIG. 5). All other serum metabolites tested were within the normal range.

Histological Analyses of Knock-In Mice

Tissues of −/− mice and their littermates were examined histologically between age P2 and P3. Particular attention was paid to skeletal muscle, heart and liver; no abnormalities were identified in these tissues. Moreover, immuno-histochemical staining with antibodies against laminin and dystrophin failed to show differences between −/− and +/+ muscle sections. The monoclonal antibodies against glycosylated α-dystroglycan and against PSA-NCAM[15] were raised in mouse, and failed to give satisfactory histological staining results.

At age P2, kidneys of −/− mice showed hemorrhages by gross examination, but were normal in size and shape compared to kidneys of +/+ and +/− littermates. Histological analyses revealed cystic dilatations in the cortex and medulla. Higher magnification views of −/− kidneys displayed collecting ducts, proximal and distal convoluted tubules, and urinary space filled with red cells and fibrillar infiltrates, indicating that blood had leaked into the tubules. The glomeruli of −/− mice contained red cell infiltrations in Bowman's space. Quantitatition of affected glomeruli in 4 mice (total of ~100 glomeruli scored) yielded 64 (±6)% affected in −/− mice versus 2 (±1) % affected in +/− and 4 (±3.5)% in +/+ mice. Immunohistochemistry with anti-GNE/MNK antibodies demonstrated localization of GNE/MNK protein to kidney glomeruli. Examinations of −/− kidneys at E18 showed no histological differences, nor developmental delay compared with normal or heterozygous littermates (not shown). Other renal disorders also become apparent only after birth, when the mice transfer from maternal to independent renal filtering of blood.

The only homozygous −/− survivor past weaning (P21) was smaller than his +/+ and +/− littermates, but he continued to grow and gain weight until about 7 months, after which he failed to grow and was sacrificed at age 8.5 months, along with two +/+ and +/− littermates. Necropsy data revealed the tubules and glomeruli contained red cell infiltrates, likely due to lesions in their epithelial linings. These renal abnormalities account for the elevated BUN levels in this mouse (FIG. 5). Detailed investigations of other tissues, in particular hindlimb and forelimb musculature, did not yield any abnormalities (structural or inflammatory). Ultrastructural analysis of −/− glomeruli revealed that the podocyte foot-process membranes were flattened and largely fused, with only a few, wide foot processes present. Filtration slits were largely reduced in number and showed formation of tight junctions. The size and shape of the glomerular basement membrane (GMB) seemed intact, with a few areas where it was reduced in size. Endothelial cells lining the basement membrane did not show ultrastructural defects. Red cells were found infiltrated in kidney tubules and were frequently odd-shaped, likely due to osmotic and/or pH environmental changes.

Rescue of the Knock-In Mice by ManNAc Feeding

ManNAc, added to the drinking water at a concentration of 1 mg/ml during matings of +/− mice did not yield any surviving homozygous mice beyond age P3 from among 51 offspring. However, at 5 mg ManNAc/ml, 11 homozygous (44% of total −/− pups) out of a total of 97 newborn pups survived beyond P3. The nursing females continued to be supplied with ManNAc until the pups were weaned (P21). Of the 11 −/− survivors past P3, 7 died after between P6 and P12, and another 2 were missing at P9. Two homozygous mice survived past P21, when ManNAc supplementation ceased. These 2 mice were smaller than their littermates, but continued to grow without receiving additional ManNAc. At 3.5 months old, one −/− survivor was sacrificed due to a debilitated physical condition. H&E histology on skeletal muscle of this mouse did not reveal any structural or inflammatory abnormalities, but the kidneys showed mild disease, including red cell infiltration in glomeruli and fibrillar inclusions in the tubules. The one surviving −/− mouse is currently 6 months old and does not exhibit apparent myopatic features.

The ManNAc treated −/− mice (and littermates) were sacrificed at age P6 to assess their tissue histology. At this age, homozygous mutated mice that could not survive past P3 were already eliminated and mice that would possibly die before weaning (age P21) were included. No abnormalities in liver, heart and skeletal muscle tissues were identified in the P6, −/−, ManNAc treated mice (not shown). Detailed histological investigations of their kidneys demonstrated a range from mildly to remarkably improved histological features. After ManNAc treatment, the number of cystic dilatations in the cortex and medulla were reduced as well as the degree of red cell infiltrates in glomeruli, in the tubular and in the urinary space. Ultrastructurally, improvement was noticeable in the severity of the fusion and flattening of the podocyte foot processes, including higher numbers of slit diaphragms and more 'finger-shaped' foot processes.

Biochemical Analyses After ManNAc Feeding

UDP-GlcNAC 2-epimerase (GNE) enzymatic activity in muscle and kidney at age P2 were determined. Compared to +/+ mice, which were set at 100% (n=4) activity, −/− mice muscle was reduced to 19 (±7)% GNE activity (n=4). Similar decreased GNE activities were measured in −/− kidney extracts (10% of normal, n=2). Upon ManNAc treatment, GNE activities in +/+ muscle increased to 114 (±10)% (n=3), while −/− muscle increased to 31 (±9)% (n=7) residual activity.

Immunoblots of muscle and kidney extracts labeled with anti-GNE/MNK antibodies demonstrated 78 (±5)% decreased amounts of GNE/MNK protein in −/− tissues, which improved in ManNAc treated muscle and kidney to 41 (±3)% decreased amounts compared to +/+ littermates (referenced to β-actin). PSA-NCAM antibodies showed a significantly increased signal of 2-28% (n=14 pre treatment and n=10 post treatment, p=0.08) in −/− brain tissues when compared to untreated −/− tissues. Staining patterns with antibodies against laminin, an integral component of the glomerular basement membrane[25], did not differ in laminin concentration or size in −/− mice kidney extracts, but antibodies against podocalyxin, the major sialoglycoprotein of the podocyte filtration slits, showed dramatically decreased sialylation in −/− kidneys. ManNAc feeding did not result in a statistically significant increase in podocalyxin sialylation status.

Example 3

Discussion

GNE gene-targeted knock-in mice was created mimicking the M712T mutation of Persian-Jewish HIBM patients. Homozygous mutated mice progressed through embryonic life at a frequency predicted by Mendelian genetics, but, except for one anomalous male, did not survive past age P3. Histological studies on −/− mice showed no muscle pathology at age P2, but skeletal muscle and kidney GNE/MNK epimerase activity was one-fifth that of their normal littermates. These decreases could partly be due to reduced presence of GNE/MNK protein in −/− tissues.

At P2, kidney histology of −/− mice revealed glomerular disease, hemorrhages, and red cells and fibrillar infiltrates in renal tubules, glomeruli, urinary space, and Bowman's space. Electron micrographs of −/− glomeruli showed dramatically flattened and fused foot processes of podocytes with severely affected filter slits. This kidney involvement was unexpected, but pointed to the critical role of sialic acid in renal tissue. On immunohistochemistry, GNE/MNK localized to kidney glomeruli, where sialic acid is abundantly present. These large amounts of sialic acid may support the extensive sialylation of glycoproteins (such as α-dystroglycan, α3β1-integrin and podocalyxin) essential for the function of podocyte foot processes. Podocytes are renal glomerular epithelial cells that provide the architecture of the glomerular filtration apparatus, including interdigitating foot processes, slit diaphragms, and the intercellular urinary spaces. The negatively charged sialic acid residues on glycoproteins act as antiadhesion molecules, assisting in maintaining an open urinary space, filtration slits and Bowman's space. Some forms of glomerular disease (such as minimal change nephrosis) can result from hyposialylation and subsequent deformation of podocyte membranes and the onset of proteinuria. Indeed, we demonstrated hyposialylated podocalyxin in −/− mice kidney extracts and electron micrographs showed flattening and fused foot processes lining the GBM, resulting in reduced numbers and malformed (forming tight junctions) filtration slits. The GBM appeared unaffected but displayed occasional thinner areas, which could be locations where red cells gained access to Bowman's space, as is seen in thin membrane disease or Alport syndrome. These severe renal findings in our −/− mice likely led to dehydration, other uremic complications, and death before age P3. Unexpectedly, this animal model might provide an opportunity to study basic mechanisms and targeted therapies of podocyte injuries, for which appropriate model systems are sparse.

Our murine findings were in contrast to the exclusively myopathic involvement in human HIBM. The early death of −/− mice did not allow for studying a possible muscular phenotype at an older age, but at P2, hyposialylation of α-dystroglycan, reported in human HIBM muscle, was not observed in −/− mouse muscle. There are several possible reasons for this. Glycosylation patterns of α-dystroglycan are complex and tissue-specific, and might also be species-specific. Renal physiology and kidney sialic acid metabolism might also differ between humans and mice. The kidney harbors specialized biosynthetic machinery for protein polysialylation, and the type of sialic acid present in human and mouse kidneys might differ. Most mammalian species utilize the sialic acid Neu5Gc (N-glycolylneuraminic acid), rather than Neu5Ac. However, humans have lost the ability to synthesize NeuGc, and rely on Neu5Ac as their main sialic acid. Mice not only have relatively little Neu5Ac, they also have negligible ability to deaminate Neu5Ac to form KDN (2-keto-3-deoxy-D-glycero-D-galacto-nonulosonic acid). In kidney, KDN predominantly decorates O-linked glycans on megalin, a membrane glycoprotein abundant in the renal proximal tubule. It is also possible that the C57BL/6 genetic background of our murine model has a high susceptibility for renal defects. Future studies, such as outbreeding our mice to a different genetic background or employing the Cre-Lox system to create conditional GNE knock-outs, might shed light on these issues.

The −/− mice did exhibit an adverse biochemical effect of decreased sialic acid production, albeit not in kidney or muscle tissue. Immunoblotting of brain extracts showed hyposialylation of PSA-NCAM in the majority of the −/− mice. Hyposyialylation of PSA-NCAM was previously reported in embryonic stem cells of complete GNE knock-out mice, as well as in skeletal muscle tissue of HIBM patients.

Whatever the reason for the early death of the M712T homozygous mice, we were able to rescue this phenotype by administering ManNAc (1 g/kg/day) to +/− breeding pairs. In fact, 42% of the −/− offspring survived past P3 and 18% of these survivors lived past weaning age P21. Histological studies at age P6 showed mildly to significantly improved kidney histology as well as increased sialylation on brain PSA-NCAM. Two mice surviving past P21, no longer supplied with ManNAc, were smaller and lighter than their littermates, but continued to grow.

Remarkably, ManNAc supplementation increased skeletal muscle GNE/MNK epimerase activity from 100% to ~114% in +/+ mice, and from 19% to 31% in −/− mice. In addition, immunoblotting revealed an increased amount of GNE/MNK protein subsequent to ManNAc feeding. These findings suggest that ManNAc might stabilize both the normal and the mutant enzymes, increasing catalytic activity. Similar stabilization effects on other proteins have been demonstrated using natural or artificial ligands or chaperones. The effects of ManNAc on GNE mutations other than M712T, are worth future investigations.

The M712T GNE knock-in mouse, despite its lack of early myopathic features, nevertheless provides a suitable model for human HIBM. First, the human disease also lacks early muscle impairment, and the M712T mouse may prove to display HIBM-like myopathy if it can be maintained well past weaning. Second, survival of the M712T mouse past P3 can serve as an absolute outcome parameter for potential therapeutic interventions, and resolution of renal disease provides a graded measure of response.

In fact, both of these outcome measures indicated a significant salutary effect of ManNAc supplementation in the M712T mouse. Although the exact mechanism of ManNAc's beneficial effect has not been proven, the apparent stabilization of UDP-GlcNAc 2-epimerase activity, combined with the known existence of ancillary enzymes providing ManNAc kinase activity, suggests that increased ManNAc supplementation is effecting increased sialic acid production. Indeed, there appears to be more sialylated PSA-NCAM in the brains of ManNAc-treated compared with untreated knock-in mice. These findings support the hypothesis that the provision of sialic acid may improve the myopathy of HIBM. Indeed, preliminary evidence indicates a mild, transient, but significant improvement in the muscle strength of HIBM patients who received intravenous immune globulin G, and it is hypothesized that this effect is mediated through the large sialic acid content provided by the immune globulin. We think that the uncharged, physiological monosaccharide ManNAc is a promising candidate-drug for a clinical trial in patients with HIBM, in particular those patients harboring the M712T GNE mutation. Other sialic acid precursors may also be reasonable candidates, especially if they show efficacy in the appropriate mouse model of HIBM.

REFERENCES

The following references are incorporated by reference herein in their entirety:

1. Schwarzkopf, M. et al. Sialylation is essential for early development in mice. Proc. Natl. Acad. Sci. U.S.A. 99, 5267-5270 (2002).

2. Luchansky, S. J., Yarema, K. J., Takahashi, S. & Bertozzi, C. R. GlcNAc 2-epimerase can serve a catabolic role in sialic acid metabolism. J. Biol. Chem. 278, 8035-8042 (2003).

3. Charter, N. W., Koshland, D. E. Jr. & Bertozzi, C. R. Biosynthetic incorporation of unnatural sialic acids into polysialic acid on neural cells. Glycobiology 10, 1049-1056 (2000).

---

What is claimed is:

1. A method of treating Hereditary Inclusion Body Myopathy (HIBM) in a subject comprising orally administering to a subject in need of such treatment an effective amount of free sialic acid or pharmaceutically acceptable salt thereof to attenuate hyposialylation in HIBM muscle.

2. The method of claim 1, wherein the subject is exhibiting myopathic symptoms.

3. A method of treating hyposialylation in skeletal muscle in a subject comprising orally administering to a subject in need of such treatment an effective amount of free sialic acid or pharmaceutically acceptable salt thereof.

4. The method of claim 3, wherein the subject is experiencing myopathic symptoms.

* * * * *

SEQUENCE LISTING

<160> NUMBER OF SEQ ID NOS: 24

<210> SEQ ID NO 1
<211> LENGTH: 2169
<212> TYPE: DNA
<213> ORGANISM: Homo sapiens

<400> SEQUENCE: 1

| | | | | | |
|---|---|---|---|---|---|
| atggagaaga | atggaaataa | ccgaaagctg | cgggtttgtg | ttgctacttg | taaccgtgca | 60 |
| gattattcta | aacttgcccc | gatcatgttt | ggcattaaaa | ccgaacctga | gttctttgaa | 120 |
| cttgatgttg | tggtacttgg | ctctcacctg | atagatgact | atggaaatac | atatcgaatg | 180 |
| attgaacaag | atgactttga | cattaacacc | aggctacaca | caattgtgag | gggagaagat | 240 |
| gaggcagcca | tggtggagtc | agtaggcctg | gccctagtga | agctgccaga | tgtccttaat | 300 |
| cgcctgaagc | ctgatatcat | gattgttcat | ggagacaggt | tgatgccct | ggctctggcc | 360 |
| acatctgctg | ccttgatgaa | catccgaatc | cttcacattg | aaggtgggga | agtcagtggg | 420 |
| accattgatg | actctatcag | acatgccata | acaaaactgg | ctcattatca | tgtgtgctgc | 480 |
| acccgcagtg | cagagcagca | cctgatatcc | atgtgtgagg | accatgatcg | catccttttg | 540 |
| gcaggctgcc | cttcctatga | caaacttctc | tcagccaaga | acaaagacta | catgagcatc | 600 |
| attcgcatgt | ggctaggtga | tgatgtaaaa | tctaaagatt | acattgttgc | actacagcac | 660 |

-continued

| | |
|---|---|
| cctgtgacca ctgacattaa gcattccata aaaatgtttg aattaacatt ggatgcactt | 720 |
| atctcattta acaagcggac cctagtcctg tttccaaata ttgacgcagg gagcaaagag | 780 |
| atggttcgag tgatgcggaa gaagggcatt gagcatcatc ccaactttcg tgcagttaaa | 840 |
| cacgtcccat ttgaccagtt tatacagttg gttgcccatg ctggctgtat gattgggaac | 900 |
| agcagctgtg gggttcgaga agttggagct tttggaacac ctgtgatcaa cctgggaaca | 960 |
| cgtcagattg aagagaaac aggggagaat gttcttcatg tccgggatgc tgacacccaa | 1020 |
| gacaaaatat tgcaagcact gcaccttcag tttggtaaac agtacccttg ttcaaagata | 1080 |
| tatggggatg aaatgctgt tccaaggatt tgaagtttc tcaaatctat cgatcttcaa | 1140 |
| gagccactgc aaaagaaatt ctgctttcct cctgtgaagg agaatatctc tcaagatatt | 1200 |
| gaccatattc ttgaaactct aagtgccttg gccgttgatc ttggcgggac gaacctccga | 1260 |
| gttgcaatag tcagcatgaa gggtgaaata gttaagaagt atactcagtt caatcctaaa | 1320 |
| acctatgaag agaggattaa tttaatccta cagatgtgtg tggaagctgc agcagaagct | 1380 |
| gtaaaactga actgcagaat tttgggagta ggcatttcca caggtggccg tgtaaatcct | 1440 |
| cgggaaggaa ttgtgctgca ttcaaccaaa ctgatccaag agtggaactc tgtggacctt | 1500 |
| aggaccccc tttctgacac tttgcatctc cctgtgtggg tagacaatga tggcaactgt | 1560 |
| gctgccctgg cggaaaggaa atttggccaa ggaaagggac tggaaaactt tgttacactt | 1620 |
| atcacaggca caggaatcgg tggtggaatt atccatcagc atgaattgat ccacggaagc | 1680 |
| tccttctgtg ctgcagaact gggccacctt gttgtgtctc tggatgggcc tgattgttcc | 1740 |
| tgtggaagcc atgggtgcat tgaagcatac gcctctggaa tggccttgca gagggaggca | 1800 |
| aaaaagctcc atgatgagga cctgctcttg gtggaaggga tgtcagtgcc aaaagatgag | 1860 |
| gctgtgggtg cgctccatct catccaagct gcgaaacttg gcaatgcgaa ggcccagagc | 1920 |
| atcctaagaa cagctggaac agctttgggt cttggggttg tgaacatcct ccataccatg | 1980 |
| aatccctccc ttgtgatcct ctccggagtc ctggccagtc actatatcca cattgtcaaa | 2040 |
| gacgtcattc gccagcaggc cttgtcctcc gtgcaggacg tggatgtggt ggtttcggat | 2100 |
| ttggttgacc ccgccctgct gggtgctgcc agcatggttc tggactacac aacacgcagg | 2160 |
| atctactag | 2169 |

<210> SEQ ID NO 2
<211> LENGTH: 722
<212> TYPE: PRT
<213> ORGANISM: Homo sapiens

<400> SEQUENCE: 2

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp

-continued

```
            100                 105                 110
Arg Phe Asp Ala Leu Ala Leu Ala Thr Ser Ala Ala Leu Met Asn Ile
            115                 120                 125
Arg Ile Leu His Ile Glu Gly Gly Glu Val Ser Gly Thr Ile Asp Asp
            130                 135             140
Ser Ile Arg His Ala Ile Thr Lys Leu Ala His Tyr His Val Cys Cys
145                 150                 155                 160
Thr Arg Ser Ala Glu Gln His Leu Ile Ser Met Cys Glu Asp His Asp
                    165                 170                 175
Arg Ile Leu Leu Ala Gly Cys Pro Ser Tyr Asp Lys Leu Leu Ser Ala
                180                 185                 190
Lys Asn Lys Asp Tyr Met Ser Ile Ile Arg Met Trp Leu Gly Asp Asp
            195                 200                 205
Val Lys Ser Lys Asp Tyr Ile Val Ala Leu Gln His Pro Val Thr Thr
            210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
                245                 250                 255
Gly Ser Lys Glu Met Val Arg Val Met Arg Lys Lys Gly Ile Glu His
                260                 265                 270
His Pro Asn Phe Arg Ala Val Lys His Val Pro Phe Asp Gln Phe Ile
            275                 280                 285
Gln Leu Val Ala His Ala Gly Cys Met Ile Gly Asn Ser Ser Cys Gly
            290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
                340                 345                 350
Lys Gln Tyr Pro Cys Ser Lys Ile Tyr Gly Asp Gly Asn Ala Val Pro
            355                 360                 365
Arg Ile Leu Lys Phe Leu Lys Ser Ile Asp Leu Gln Glu Pro Leu Gln
            370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
                420                 425                 430
Lys Tyr Thr Gln Phe Asn Pro Lys Thr Tyr Glu Glu Arg Ile Asn Leu
            435                 440                 445
Ile Leu Gln Met Cys Val Glu Ala Ala Glu Ala Val Lys Leu Asn
            450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
                500                 505                 510
Trp Val Asp Asn Asp Gly Asn Cys Ala Ala Leu Ala Glu Arg Lys Phe
            515                 520                 525
```

```
Gly Gln Gly Lys Gly Leu Glu Asn Phe Val Thr Leu Ile Thr Gly Thr
            530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
    610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr

<210> SEQ ID NO 3
<211> LENGTH: 7
<212> TYPE: PRT
<213> ORGANISM: Homo sapiens

<400> SEQUENCE: 3

Met Glu Lys Asn Gly Asn Asn
1               5

<210> SEQ ID NO 4
<211> LENGTH: 722
<212> TYPE: PRT
<213> ORGANISM: Homo sapiens

<400> SEQUENCE: 4

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Trp Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110
```

```
Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
            195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
```

```
                    530             535                 540
Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
                595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
                675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile Tyr

<210> SEQ ID NO 5
<211> LENGTH: 722
<212> TYPE: PRT
<213> ORGANISM: Homo sapiens

<400> SEQUENCE: 5

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
                35                  40                  45

His Leu Ile Asp Asp Tyr Gly Asn Thr Tyr Arg Met Ile Glu Gln Asp
                50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
                115                 120                 125

Arg Ile Leu His Ile Glu Gly Gly Glu Val Ser Gly Thr Thr Asp Asp
                130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
```

```
                180                 185                 190
Lys Asn Lys Asp Tyr Met Ser Ile Ile Arg Met Trp Leu Gly Asp Asp
            195                 200                 205

Val Lys Ser Lys Asp Tyr Ile Val Ala Leu Gln His Pro Val Thr Thr
        210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
    530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605
```

-continued

```
Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
            645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
            690                 695                 700

Ala Leu Leu Gly Ala Ala Ser Met Val Leu Asp Tyr Thr Thr Arg Arg
705                 710                 715                 720

Ile Tyr

<210> SEQ ID NO 6
<211> LENGTH: 722
<212> TYPE: PRT
<213> ORGANISM: Homo sapiens
<220> FEATURE:
<221> NAME/KEY: misc_feature
<222> LOCATION: (204)..(204)
<223> OTHER INFORMATION: Xaa can be any naturally occurring amino acid

<400> SEQUENCE: 6

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Xaa Leu Gly Asp Asp
            195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
```

```
            225                 230                 235                 240

Ile Ser Phe Asn Lys Arg Thr Leu Val Leu Phe Pro Asn Ile Asp Ala
                    245                 250                 255

Gly Ser Lys Glu Met Val Arg Val Met Arg Lys Lys Gly Ile Glu His
                    260                 265                 270

His Pro Asn Phe Arg Ala Val Lys His Val Pro Phe Asp Gln Phe Ile
                    275                 280                 285

Gln Leu Val Ala His Ala Gly Cys Met Ile Gly Asn Ser Ser Cys Gly
                290                 295                 300

Val Arg Glu Val Gly Ala Phe Gly Thr Pro Val Ile Asn Leu Gly Thr
    305                 310                 315                 320

Arg Gln Ile Gly Arg Glu Thr Gly Glu Asn Val Leu His Val Arg Asp
                    325                 330                 335

Ala Asp Thr Gln Asp Lys Ile Leu Gln Ala Leu His Leu Gln Phe Gly
                    340                 345                 350

Lys Gln Tyr Pro Cys Ser Lys Ile Tyr Gly Asp Gly Asn Ala Val Pro
                    355                 360                 365

Arg Ile Leu Lys Phe Leu Lys Ser Ile Asp Leu Gln Glu Pro Leu Gln
        370                 375                 380

Lys Lys Phe Cys Phe Pro Pro Val Lys Glu Asn Ile Ser Gln Asp Ile
    385                 390                 395                 400

Asp His Ile Leu Glu Thr Leu Ser Ala Leu Ala Val Asp Leu Gly Gly
                    405                 410                 415

Thr Asn Leu Arg Val Ala Ile Val Ser Met Lys Gly Glu Ile Val Lys
                    420                 425                 430

Lys Tyr Thr Gln Phe Asn Pro Lys Thr Tyr Glu Glu Arg Ile Asn Leu
                    435                 440                 445

Ile Leu Gln Met Cys Val Glu Ala Ala Glu Ala Val Lys Leu Asn Asn
            450                 455                 460

Cys Arg Ile Leu Gly Val Gly Ile Ser Thr Gly Gly Arg Val Asn Pro
    465                 470                 475                 480

Arg Glu Gly Ile Val Leu His Ser Thr Lys Leu Ile Gln Glu Trp Asn
                    485                 490                 495

Ser Val Asp Leu Arg Thr Pro Leu Ser Asp Thr Leu His Leu Pro Val
                    500                 505                 510

Trp Val Asp Asn Asp Gly Asn Cys Ala Ala Leu Ala Glu Arg Lys Phe
                    515                 520                 525

Gly Gln Gly Lys Gly Leu Glu Asn Phe Val Thr Leu Ile Thr Gly Thr
                530                 535                 540

Gly Ile Gly Gly Gly Ile Ile His Gln His Glu Leu Ile His Gly Ser
    545                 550                 555                 560

Ser Phe Cys Ala Ala Glu Leu Gly His Leu Val Val Ser Leu Asp Gly
                    565                 570                 575

Pro Asp Cys Ser Cys Gly Ser His Gly Cys Ile Glu Ala Tyr Ala Ser
                    580                 585                 590

Gly Met Ala Leu Gln Arg Glu Ala Lys Lys Leu His Asp Glu Asp Leu
                    595                 600                 605

Leu Leu Val Glu Gly Met Ser Val Pro Lys Asp Glu Ala Val Gly Ala
                    610                 615                 620

Leu His Leu Ile Gln Ala Ala Lys Leu Gly Asn Ala Lys Ala Gln Ser
    625                 630                 635                 640

Ile Leu Arg Thr Ala Gly Thr Ala Leu Gly Leu Gly Val Val Asn Ile
                    645                 650                 655
```

```
Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
            690                 695                 700

Ala Leu Leu Gly Ala Ala Ser Met Val Leu Asp Tyr Thr Thr Arg Arg
705                 710                 715                 720

Ile Tyr

<210> SEQ ID NO 7
<211> LENGTH: 722
<212> TYPE: PRT
<213> ORGANISM: Homo sapiens

<400> SEQUENCE: 7

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
            35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Ala Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300
```

```
Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
            325                 330                 335

Ala Asp Thr Gln Asp Lys Ile Leu Gln Ala Leu His Leu Gln Phe Gly
                340                 345                 350

Lys Gln Tyr Pro Cys Ser Lys Ile Tyr Gly Asp Gly Asn Ala Val Pro
            355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
                435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
            515                 520                 525

Gly Gln Gly Lys Gly Leu Glu Asn Phe Val Thr Leu Ile Thr Gly Thr
            530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
            645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
            690                 695                 700

Ala Leu Leu Gly Ala Ala Ser Met Val Leu Asp Tyr Thr Thr Arg Arg
705                 710                 715                 720
```

Ile Tyr

<210> SEQ ID NO 8
<211> LENGTH: 722
<212> TYPE: PRT
<213> ORGANISM: Homo sapiens

<400> SEQUENCE: 8

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Gln Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365
```

```
Arg Ile Leu Lys Phe Leu Lys Ser Ile Asp Leu Gln Glu Pro Leu Gln
            370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
                500                 505                 510

Trp Val Asp Asn Asp Gly Asn Cys Ala Ala Leu Ala Glu Arg Lys Phe
            515                 520                 525

Gly Gln Gly Lys Gly Leu Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
        690                 695                 700

Ala Leu Leu Gly Ala Ala Ser Met Val Leu Asp Tyr Thr Thr Arg Arg
705                 710                 715                 720

Ile Tyr

<210> SEQ ID NO 9
<211> LENGTH: 722
<212> TYPE: PRT
<213> ORGANISM: Homo sapiens

<400> SEQUENCE: 9

Met Glu Lys Asn Gly Asn Asn Arg Lys Leu Arg Val Cys Val Ala Thr
1               5                   10                  15
```

-continued

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
                180                 185                 190

Lys Asn Lys Asp Tyr Met Ser Ile Arg Met Trp Leu Gly Asp Asp
        195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
                260                 265                 270

His Pro Asn Phe Arg Ala Val Lys His Val Pro Phe Asp Gln Phe Ile
        275                 280                 285

Gln Leu Val Ala His Ala Gly Cys Met Thr Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
                340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
                420                 425                 430

Lys Tyr Thr Gln Phe Asn Pro Lys Thr Tyr Glu Glu Arg Ile Asn Leu

```
                435                 440                 445
Ile Leu Gln Met Cys Val Glu Ala Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                    485                 490                 495

Ser Val Asp Leu Arg Thr Pro Leu Ser Asp Thr Leu His Leu Pro Val
                500                 505                 510

Trp Val Asp Asn Asp Gly Asn Cys Ala Ala Leu Ala Glu Arg Lys Phe
            515                 520                 525

Gly Gln Gly Lys Gly Leu Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                    565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                    645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
        690                 695                 700

Ala Leu Leu Gly Ala Ala Ser Met Val Leu Asp Tyr Thr Thr Arg Arg
705                 710                 715                 720

Ile Tyr

<210> SEQ ID NO 10
<211> LENGTH: 722
<212> TYPE: PRT
<213> ORGANISM: Homo sapiens

<400> SEQUENCE: 10

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
            35                  40                  45

His Leu Ile Asp Asp Tyr Gly Asn Thr Tyr Arg Met Ile Glu Gln Asp
        50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
```

-continued

```
                 85                  90                  95
Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Trp Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510
```

```
Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
        690                 695                 700

Ala Leu Leu Gly Ala Ala Ser Met Val Leu Asp Tyr Thr Thr Arg Arg
705                 710                 715                 720

Ile Tyr

<210> SEQ ID NO 11
<211> LENGTH: 722
<212> TYPE: PRT
<213> ORGANISM: Homo sapiens
<220> FEATURE:
<221> NAME/KEY: misc_feature
<222> LOCATION: (436)..(436)
<223> OTHER INFORMATION: Xaa can be any naturally occurring amino acid

<400> SEQUENCE: 11

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
```

```
                130                 135                 140
Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
                180                 185                 190

Lys Asn Lys Asp Tyr Met Ser Ile Ile Arg Met Trp Leu Gly Asp Asp
                195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
                260                 265                 270

His Pro Asn Phe Arg Ala Val Lys His Val Pro Phe Asp Gln Phe Ile
                275                 280                 285

Gln Leu Val Ala His Ala Gly Cys Met Ile Gly Asn Ser Ser Cys Gly
                290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
                340                 345                 350

Lys Gln Tyr Pro Cys Ser Lys Ile Tyr Gly Asp Gly Asn Ala Val Pro
                355                 360                 365

Arg Ile Leu Lys Phe Leu Lys Ser Ile Asp Leu Gln Glu Pro Leu Gln
                370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
                420                 425                 430

Lys Tyr Thr Xaa Phe Asn Pro Lys Thr Tyr Glu Glu Arg Ile Asn Leu
                435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
                500                 505                 510

Trp Val Asp Asn Asp Gly Asn Cys Ala Ala Leu Ala Glu Arg Lys Phe
                515                 520                 525

Gly Gln Gly Lys Gly Leu Glu Asn Phe Val Thr Leu Ile Thr Gly Thr
                530                 535                 540

Gly Ile Gly Gly Gly Ile Ile His Gln His Glu Leu Ile His Gly Ser
545                 550                 555                 560
```

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
    610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
        690                 695                 700

Ala Leu Leu Gly Ala Ala Ser Met Val Leu Asp Tyr Thr Thr Arg Arg
705                 710                 715                 720

Ile Tyr

<210> SEQ ID NO 12
<211> LENGTH: 722
<212> TYPE: PRT
<213> ORGANISM: Homo sapiens

<400> SEQUENCE: 12

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

```
Val Lys Ser Lys Asp Tyr Ile Val Ala Leu Gln His Pro Val Thr Thr
    210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
                245                 250                 255
Gly Ser Lys Glu Met Val Arg Val Met Arg Lys Gly Ile Glu His
                260                 265                 270
His Pro Asn Phe Arg Ala Val Lys His Val Pro Phe Asp Gln Phe Ile
            275                 280                 285
Gln Leu Val Ala His Ala Gly Cys Met Ile Gly Asn Ser Ser Cys Gly
    290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
                340                 345                 350
Lys Gln Tyr Pro Cys Ser Lys Ile Tyr Gly Asp Gly Asn Ala Val Pro
    355                 360                 365
Arg Ile Leu Lys Phe Leu Lys Ser Ile Asp Leu Gln Glu Pro Leu Gln
370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
                420                 425                 430
Lys Tyr Thr Gln Phe Asn Pro Lys Thr Tyr Glu Glu Arg Ile Asn Leu
            435                 440                 445
Ile Leu Gln Met Cys Val Glu Ala Ala Glu Ala Val Lys Leu Asn
    450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
                500                 505                 510
Trp Val Asp Asn Asp Gly Asn Cys Ala Ala Leu Ala Glu Arg Lys Phe
            515                 520                 525
Gly Gln Gly Lys Gly Leu Glu Asn Phe Val Thr Leu Ile Thr Gly Thr
    530                 535                 540
Gly Ile Gly Gly Gly Ile Ile His Gln His Glu Ser Ile His Gly Ser
545                 550                 555                 560
Ser Phe Cys Ala Ala Glu Leu Gly His Leu Val Val Ser Leu Asp Gly
                565                 570                 575
Pro Asp Cys Ser Cys Gly Ser His Gly Cys Ile Glu Ala Tyr Ala Ser
                580                 585                 590
Gly Met Ala Leu Gln Arg Glu Ala Lys Lys Leu His Asp Glu Asp Leu
            595                 600                 605
Leu Leu Val Glu Gly Met Ser Val Pro Lys Asp Glu Ala Val Gly Ala
    610                 615                 620
```

```
Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
            645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile Tyr
```

<210> SEQ ID NO 13
<211> LENGTH: 722
<212> TYPE: PRT
<213> ORGANISM: Homo sapiens

<400> SEQUENCE: 13

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
            35                  40                  45

His Leu Ile Asp Asp Tyr Gly Asn Thr Tyr Arg Met Ile Glu Gln Asp
50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270
```

```
His Pro Asn Phe Arg Ala Val Lys His Val Pro Asp Gln Phe Ile
            275                 280                 285

Gln Leu Val Ala His Ala Gly Cys Met Ile Gly Asn Ser Ser Cys Gly
290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
```

```
                    690                 695                 700
Ala Leu Leu Gly Ala Ala Ser Met Val Leu Asp Tyr Thr Thr Arg Arg
705                 710                 715                 720

Ile Tyr

<210> SEQ ID NO 14
<211> LENGTH: 722
<212> TYPE: PRT
<213> ORGANISM: Homo sapiens

<400> SEQUENCE: 14

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Leu Gly Ser
            35                  40                  45

His Leu Ile Asp Asp Tyr Gly Asn Thr Tyr Arg Met Ile Glu Gln Asp
        50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
```

```
                340             345             350
Lys Gln Tyr Pro Cys Ser Lys Ile Tyr Gly Asp Gly Asn Ala Val Pro
            355                 360                 365
Arg Ile Leu Lys Phe Leu Lys Ser Ile Asp Leu Gln Glu Pro Leu Gln
        370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
            420                 425                 430
Lys Tyr Thr Gln Phe Asn Pro Lys Thr Tyr Glu Glu Arg Ile Asn Leu
        435                 440                 445
Ile Leu Gln Met Cys Val Glu Ala Ala Glu Ala Val Lys Leu Asn
450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
            500                 505                 510
Trp Val Asp Asn Asp Gly Asn Cys Ala Ala Leu Ala Glu Arg Lys Phe
        515                 520                 525
Gly Gln Gly Lys Gly Leu Glu Asn Phe Val Thr Leu Ile Thr Gly Thr
    530                 535                 540
Gly Ile Gly Gly Gly Ile Ile His Gln His Glu Leu Ile His Gly Ser
545                 550                 555                 560
Ser Phe Cys Ala Ala Glu Leu Gly His Leu Val Val Ser Leu Asp Gly
                565                 570                 575
Pro Asp Cys Ser Cys Gly Ser His Gly Cys Thr Glu Ala Tyr Ala Ser
            580                 585                 590
Gly Met Ala Leu Gln Arg Glu Ala Lys Lys Leu His Asp Glu Asp Leu
        595                 600                 605
Leu Leu Val Glu Gly Met Ser Val Pro Lys Asp Glu Ala Val Gly Ala
    610                 615                 620
Leu His Leu Ile Gln Ala Ala Lys Leu Gly Asn Ala Lys Ala Gln Ser
625                 630                 635                 640
Ile Leu Arg Thr Ala Gly Thr Ala Leu Gly Leu Gly Val Val Asn Ile
                645                 650                 655
Leu His Thr Met Asn Pro Ser Leu Val Ile Leu Ser Gly Val Leu Ala
            660                 665                 670
Ser His Tyr Ile His Ile Val Lys Asp Val Ile Arg Gln Gln Ala Leu
        675                 680                 685
Ser Ser Val Gln Asp Val Asp Val Val Ser Asp Leu Val Asp Pro
    690                 695                 700
Ala Leu Leu Gly Ala Ala Ser Met Val Leu Asp Tyr Thr Thr Arg Arg
705                 710                 715                 720
Ile Tyr

<210> SEQ ID NO 15
<211> LENGTH: 722
<212> TYPE: PRT
<213> ORGANISM: Homo sapiens
<220> FEATURE:
```

<221> NAME/KEY: misc_feature
<222> LOCATION: (615)..(615)
<223> OTHER INFORMATION: Xaa can be any naturally occurring amino acid

<400> SEQUENCE: 15

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
```

```
                385                 390                 395                 400
        Asp His Ile Leu Glu Thr Leu Ser Ala Leu Ala Val Asp Leu Gly Gly
                            405                 410                 415

Thr Asn Leu Arg Val Ala Ile Val Ser Met Lys Gly Glu Ile Val Lys
                        420                 425                 430

Lys Tyr Thr Gln Phe Asn Pro Lys Thr Tyr Glu Glu Arg Ile Asn Leu
                        435                 440                 445

Ile Leu Gln Met Cys Val Glu Ala Ala Glu Ala Val Lys Leu Asn
            450                 455                 460

Cys Arg Ile Leu Gly Val Gly Ile Ser Thr Gly Gly Arg Val Asn Pro
        465                 470                 475                 480

Arg Glu Gly Ile Val Leu His Ser Thr Lys Leu Ile Gln Glu Trp Asn
                            485                 490                 495

Ser Val Asp Leu Arg Thr Pro Leu Ser Asp Thr Leu His Leu Pro Val
                        500                 505                 510

Trp Val Asp Asn Asp Gly Asn Cys Ala Ala Leu Ala Glu Arg Lys Phe
                    515                 520                 525

Gly Gln Gly Lys Gly Leu Glu Asn Phe Val Thr Leu Ile Thr Gly Thr
                    530                 535                 540

Gly Ile Gly Gly Gly Ile Ile His Gln His Glu Leu Ile His Gly Ser
        545                 550                 555                 560

Ser Phe Cys Ala Ala Glu Leu Gly His Leu Val Val Ser Leu Asp Gly
                            565                 570                 575

Pro Asp Cys Ser Cys Gly Ser His Gly Cys Ile Glu Ala Tyr Ala Ser
                        580                 585                 590

Gly Met Ala Leu Gln Arg Glu Ala Lys Lys Leu His Asp Glu Asp Leu
                        595                 600                 605

Leu Leu Val Glu Gly Met Xaa Val Pro Lys Asp Glu Ala Val Gly Ala
                        610                 615                 620

Leu His Leu Ile Gln Ala Ala Lys Leu Gly Asn Ala Lys Ala Gln Ser
        625                 630                 635                 640

Ile Leu Arg Thr Ala Gly Thr Ala Leu Gly Leu Gly Val Val Asn Ile
                            645                 650                 655

Leu His Thr Met Asn Pro Ser Leu Val Ile Leu Ser Gly Val Leu Ala
                        660                 665                 670

Ser His Tyr Ile His Ile Val Lys Asp Val Ile Arg Gln Gln Ala Leu
                    675                 680                 685

Ser Ser Val Gln Asp Val Asp Val Val Ser Asp Leu Val Asp Pro
                    690                 695                 700

Ala Leu Leu Gly Ala Ala Ser Met Val Leu Asp Tyr Thr Thr Arg Arg
        705                 710                 715                 720

Ile Tyr

<210> SEQ ID NO 16
<211> LENGTH: 722
<212> TYPE: PRT
<213> ORGANISM: Homo sapiens

<400> SEQUENCE: 16

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Val Leu Gly Ser
```

```
              35                  40                  45
His Leu Ile Asp Asp Tyr Gly Asn Thr Tyr Arg Met Ile Glu Gln Asp
 50                  55                  60

Asp Phe Asp Ile Asn Thr Arg Leu His Thr Ile Val Arg Gly Glu Asp
 65                  70                  75                  80

Glu Ala Ala Met Val Glu Ser Val Gly Leu Ala Leu Val Lys Leu Pro
                 85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
                115                 120                 125

Arg Ile Leu His Ile Glu Gly Gly Glu Val Ser Gly Thr Ile Asp Asp
            130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
                180                 185                 190

Lys Asn Lys Asp Tyr Met Ser Ile Ile Arg Met Trp Leu Gly Asp Asp
            195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
            275                 280                 285

Gln Leu Val Ala His Ala Gly Cys Met Ile Gly Asn Ser Ser Cys Gly
290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
            325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
            355                 360                 365

Arg Ile Leu Lys Phe Leu Lys Ser Ile Asp Leu Gln Glu Pro Leu Gln
            370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
                420                 425                 430

Lys Tyr Thr Gln Phe Asn Pro Lys Thr Tyr Glu Glu Arg Ile Asn Leu
            435                 440                 445

Ile Leu Gln Met Cys Val Glu Ala Ala Glu Ala Val Lys Leu Asn
450                 455                 460
```

```
Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
    530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
610                 615                 620

Leu His Leu Ile Gln Ala Val Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr

<210> SEQ ID NO 17
<211> LENGTH: 722
<212> TYPE: PRT
<213> ORGANISM: Homo sapiens

<400> SEQUENCE: 17

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
            35                  40                  45

His Leu Ile Asp Asp Tyr Gly Asn Thr Tyr Arg Met Ile Glu Gln Asp
        50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110
```

-continued

```
Arg Phe Asp Ala Leu Ala Leu Ala Thr Ser Ala Ala Leu Met Asn Ile
        115                 120                 125
Arg Ile Leu His Ile Glu Gly Glu Val Ser Gly Thr Ile Asp Asp
    130                 135                 140
Ser Ile Arg His Ala Ile Thr Lys Leu Ala His Tyr His Val Cys Cys
145                 150                 155                 160
Thr Arg Ser Ala Glu Gln His Leu Ile Ser Met Cys Glu Asp His Asp
                165                 170                 175
Arg Ile Leu Leu Ala Gly Cys Pro Ser Tyr Asp Lys Leu Leu Ser Ala
            180                 185                 190
Lys Asn Lys Asp Tyr Met Ser Ile Ile Arg Met Trp Leu Gly Asp Asp
        195                 200                 205
Val Lys Ser Lys Asp Tyr Ile Val Ala Leu Gln His Pro Val Thr Thr
    210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
                245                 250                 255
Gly Ser Lys Glu Met Val Arg Val Met Arg Lys Gly Ile Glu His
            260                 265                 270
His Pro Asn Phe Arg Ala Val Lys His Val Pro Phe Asp Gln Phe Ile
        275                 280                 285
Gln Leu Val Ala His Ala Gly Cys Met Ile Gly Asn Ser Ser Cys Gly
    290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
            340                 345                 350
Lys Gln Tyr Pro Cys Ser Lys Ile Tyr Gly Asp Gly Asn Ala Val Pro
        355                 360                 365
Arg Ile Leu Lys Phe Leu Lys Ser Ile Asp Leu Gln Glu Pro Leu Gln
    370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
            420                 425                 430
Lys Tyr Thr Gln Phe Asn Pro Lys Thr Tyr Glu Glu Arg Ile Asn Leu
        435                 440                 445
Ile Leu Gln Met Cys Val Glu Ala Ala Glu Ala Val Lys Leu Asn
    450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
            500                 505                 510
Trp Val Asp Asn Asp Gly Asn Cys Ala Ala Leu Ala Glu Arg Lys Phe
        515                 520                 525
```

```
Gly Gln Gly Lys Gly Leu Glu Asn Phe Val Thr Leu Ile Thr Gly Thr
            530                 535                 540

Gly Ile Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile Tyr
```

<210> SEQ ID NO 18
<211> LENGTH: 722
<212> TYPE: PRT
<213> ORGANISM: Homo sapiens

<400> SEQUENCE: 18

```
Met Glu Lys Asn Gly Asn Asn Arg Lys Leu Arg Val Cys Val Ala Thr
1                   5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
                35                  40                  45

His Leu Ile Asp Asp Tyr Gly Asn Thr Tyr Arg Met Ile Glu Gln Asp
        50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175
```

```
Arg Ile Leu Leu Ala Gly Cys Pro Ser Tyr Asp Lys Leu Leu Ser Ala
            180                 185                 190
Lys Asn Lys Asp Tyr Met Ser Ile Ile Arg Met Trp Leu Gly Asp Asp
        195                 200                 205
Val Lys Ser Lys Asp Tyr Ile Val Ala Leu Gln His Pro Val Thr Thr
    210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
                245                 250                 255
Gly Ser Lys Glu Met Val Arg Val Met Arg Lys Lys Gly Ile Glu His
            260                 265                 270
His Pro Asn Phe Arg Ala Val Lys His Val Pro Phe Asp Gln Phe Ile
        275                 280                 285
Gln Leu Val Ala His Ala Gly Cys Met Ile Gly Asn Ser Ser Cys Gly
    290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
            340                 345                 350
Lys Gln Tyr Pro Cys Ser Lys Ile Tyr Gly Asp Gly Asn Ala Val Pro
        355                 360                 365
Arg Ile Leu Lys Phe Leu Lys Ser Ile Asp Leu Gln Glu Pro Leu Gln
    370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
            420                 425                 430
Lys Tyr Thr Gln Phe Asn Pro Lys Thr Tyr Glu Glu Arg Ile Asn Leu
        435                 440                 445
Ile Leu Gln Met Cys Val Glu Ala Ala Glu Ala Val Lys Leu Asn
    450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
            500                 505                 510
Trp Val Asp Asn Asp Gly Asn Cys Ala Ala Leu Ala Glu Arg Lys Phe
        515                 520                 525
Gly Gln Gly Lys Gly Leu Glu Asn Phe Val Thr Leu Ile Thr Gly Thr
    530                 535                 540
Gly Ile Gly Gly Gly Ile Ile His Gln His Glu Leu Ile His Gly Ser
545                 550                 555                 560
Ser Phe Cys Ala Ala Glu Leu Gly His Leu Val Val Ser Leu Asp Gly
                565                 570                 575
Pro Asp Cys Ser Cys Gly Ser His Gly Cys Ile Glu Ala Tyr Ala Ser
            580                 585                 590
Gly Met Ala Leu Gln Arg Glu Ala Lys Lys Leu His Asp Glu Asp Leu
```

```
                595                 600                 605
Leu Leu Val Glu Gly Met Ser Val Pro Lys Asp Glu Ala Val Gly Ala
610                 615                 620
Leu His Leu Ile Gln Ala Ala Lys Leu Gly Asn Ala Lys Ala Gln Ser
625                 630                 635                 640
Ile Leu Arg Thr Ala Gly Thr Ala Leu Gly Leu Gly Val Val Asn Ile
                645                 650                 655
Leu His Thr Met Asn Pro Ser Leu Val Ile Leu Ser Gly Val Leu Ala
                660                 665                 670
Ser His Tyr Ile His Ile Val Lys Asp Val Ile Arg Gln Gln Ala Leu
                675                 680                 685
Ser Ser Val Gln Asp Val Asp Met Val Val Ser Asp Leu Val Asp Pro
690                 695                 700
Ala Leu Leu Gly Ala Ala Ser Met Val Leu Asp Tyr Thr Thr Arg Arg
705                 710                 715                 720
Ile Tyr

<210> SEQ ID NO 19
<211> LENGTH: 722
<212> TYPE: PRT
<213> ORGANISM: Homo sapiens

<400> SEQUENCE: 19

Met Glu Lys Asn Gly Asn Asn Arg Lys Leu Arg Val Cys Val Ala Thr
1               5                   10                  15
Cys Asn Arg Ala Asp Tyr Ser Lys Leu Ala Pro Ile Met Phe Gly Ile
                20                  25                  30
Lys Thr Glu Pro Glu Phe Phe Glu Leu Asp Val Val Val Leu Gly Ser
                35                  40                  45
His Leu Ile Asp Asp Tyr Gly Asn Thr Tyr Arg Met Ile Glu Gln Asp
50                  55                  60
Asp Phe Asp Ile Asn Thr Arg Leu His Thr Ile Val Arg Gly Glu Asp
65                  70                  75                  80
Glu Ala Ala Met Val Glu Ser Val Gly Leu Ala Leu Val Lys Leu Pro
                85                  90                  95
Asp Val Leu Asn Arg Leu Lys Pro Asp Ile Met Ile Val His Gly Asp
                100                 105                 110
Arg Phe Asp Ala Leu Ala Leu Ala Thr Ser Ala Ala Leu Met Asn Ile
                115                 120                 125
Arg Ile Leu His Ile Glu Gly Gly Glu Val Ser Gly Thr Ile Asp Asp
                130                 135                 140
Ser Ile Arg His Ala Ile Thr Lys Leu Ala His Tyr His Val Cys Cys
145                 150                 155                 160
Thr Arg Ser Ala Glu Gln His Leu Ile Ser Met Cys Glu Asp His Asp
                165                 170                 175
Arg Ile Leu Leu Ala Gly Cys Pro Ser Tyr Asp Lys Leu Leu Ser Ala
                180                 185                 190
Lys Asn Lys Asp Tyr Met Ser Ile Ile Arg Met Trp Leu Gly Asp Asp
                195                 200                 205
Val Lys Ser Lys Asp Tyr Ile Val Ala Leu Gln His Pro Val Thr Thr
                210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
```

-continued

```
               245                 250                 255
Gly Ser Lys Glu Met Val Arg Val Met Arg Lys Lys Gly Ile Glu His
            260                 265                 270
His Pro Asn Phe Arg Ala Val Lys His Val Pro Phe Asp Gln Phe Ile
            275                 280                 285
Gln Leu Val Ala His Ala Gly Cys Met Ile Gly Asn Ser Ser Cys Gly
            290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
                340                 345                 350
Lys Gln Tyr Pro Cys Ser Lys Ile Tyr Gly Asp Gly Asn Ala Val Pro
            355                 360                 365
Arg Ile Leu Lys Phe Leu Lys Ser Ile Asp Leu Gln Glu Pro Leu Gln
            370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
            420                 425                 430
Lys Tyr Thr Gln Phe Asn Pro Lys Thr Tyr Glu Glu Arg Ile Asn Leu
            435                 440                 445
Ile Leu Gln Met Cys Val Glu Ala Ala Glu Ala Val Lys Leu Asn
            450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
            500                 505                 510
Trp Val Asp Asn Asp Gly Asn Cys Ala Ala Leu Ala Glu Arg Lys Phe
            515                 520                 525
Gly Gln Gly Lys Gly Leu Glu Asn Phe Val Thr Leu Ile Thr Gly Thr
            530                 535                 540
Gly Ile Gly Gly Gly Ile Ile His Gln His Glu Leu Ile His Gly Ser
545                 550                 555                 560
Ser Phe Cys Ala Ala Glu Leu Gly His Leu Val Val Ser Leu Asp Gly
                565                 570                 575
Pro Asp Cys Ser Cys Gly Ser His Gly Cys Ile Glu Ala Tyr Ala Ser
            580                 585                 590
Gly Met Ala Leu Gln Arg Glu Ala Lys Lys Leu His Asp Glu Asp Leu
            595                 600                 605
Leu Leu Val Glu Gly Met Ser Val Pro Lys Asp Glu Ala Val Gly Ala
            610                 615                 620
Leu His Leu Ile Gln Ala Ala Lys Leu Gly Asn Ala Lys Ala Gln Ser
625                 630                 635                 640
Ile Leu Arg Thr Ala Gly Thr Ala Leu Gly Leu Gly Val Val Asn Ile
                645                 650                 655
Leu His Thr Met Asn Pro Ser Leu Val Ile Leu Ser Gly Val Leu Ala
                660                 665                 670
```

```
Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
    690                 695                 700

Ala Leu Leu Gly Ala Ala Ser Thr Val Leu Asp Tyr Thr Thr Arg Arg
705                 710                 715                 720

Ile Tyr

<210> SEQ ID NO 20
<211> LENGTH: 21
<212> TYPE: DNA
<213> ORGANISM: Homo sapiens

<400> SEQUENCE: 20
agcacttcct ggagtttgat g                                          21

<210> SEQ ID NO 21
<211> LENGTH: 24
<212> TYPE: DNA
<213> ORGANISM: Homo sapiens

<400> SEQUENCE: 21
atttgccttc gcagaaacac ttga                                       24

<210> SEQ ID NO 22
<211> LENGTH: 20
<212> TYPE: DNA
<213> ORGANISM: Homo sapiens

<400> SEQUENCE: 22
gcccagagca tcttacgaac                                            20

<210> SEQ ID NO 23
<211> LENGTH: 18
<212> TYPE: DNA
<213> ORGANISM: Homo sapiens

<400> SEQUENCE: 23
gggtcccctg gagcttgg                                              18

<210> SEQ ID NO 24
<211> LENGTH: 20
<212> TYPE: PRT
<213> ORGANISM: Homo sapiens

<400> SEQUENCE: 24

Glu Ala Tyr Ala Ser Gly Met Ala Leu Gln Arg Glu Ala Lys Lys Leu
1               5                   10                  15

His Asp Glu Asp
            20
```